US009241683B2

(12) United States Patent
Slayton et al.

(10) Patent No.: US 9,241,683 B2
(45) Date of Patent: Jan. 26, 2016

(54) ULTRASOUND SYSTEM AND METHOD FOR IMAGING AND/OR MEASURING DISPLACEMENT OF MOVING TISSUE AND FLUID

(75) Inventors: Michael H. Slayton, Tempe, AZ (US); Vadim Kouklev, Tempe, AZ (US); Peter G. Barthe, Phoenix, AZ (US); Paul Jaeger, Mesa, AZ (US)

(73) Assignee: Ardent Sound Inc., Mesa, AZ (US)

( * ) Notice: Subject to any disclaimer, the term of this patent is extended or adjusted under 35 U.S.C. 154(b) by 915 days.

(21) Appl. No.: 11/538,794

(22) Filed: Oct. 4, 2006

(65) Prior Publication Data

US 2008/0086054 A1    Apr. 10, 2008

(51) Int. Cl.
*A61B 8/08* (2006.01)
*A61B 8/06* (2006.01)
*A61B 8/13* (2006.01)

(52) U.S. Cl.
CPC ... *A61B 8/08* (2013.01); *A61B 8/06* (2013.01); *A61B 8/13* (2013.01); *A61B 8/488* (2013.01)

(58) Field of Classification Search
USPC ........... 600/438, 437, 440, 441; 345/501–503
See application file for complete search history.

(56) References Cited

U.S. PATENT DOCUMENTS

| | | | |
|---|---|---|---|
| 3,913,386 A | 10/1975 | Saglio | |
| 3,965,455 A | 6/1976 | Hurwitz | |
| 3,992,925 A | 11/1976 | Perilhou | |
| 4,039,312 A | 8/1977 | Patru | |
| 4,059,098 A | 11/1977 | Murdock | |
| 4,101,795 A | 7/1978 | Fukumoto et al. | |
| 4,213,344 A | 7/1980 | Rose | |
| 4,276,491 A | 6/1981 | Daniel | |
| 4,315,514 A | 2/1982 | Drewes et al. | |
| 4,325,381 A | 4/1982 | Glenn | |
| 4,343,301 A | 8/1982 | Indech | |
| 4,372,296 A | 2/1983 | Fahim | |
| 4,381,007 A | 4/1983 | Doss | |
| 4,381,787 A | 5/1983 | Hottinger | |

(Continued)

FOREIGN PATENT DOCUMENTS

| | | |
|---|---|---|
| DE | 4029175 | 3/1992 |
| DE | 10140064 | 3/2003 |

(Continued)

OTHER PUBLICATIONS

I. Makin et al, B-Scan Imaging and Thermal Lesion Monitoring Using Miniaturized Dual-Functionality Ultrasound Arrays, Ultrasonics Symposium, Aug. 23, 2004, pp. 1788-1791, 2004 IEEE vol. 3.

(Continued)

*Primary Examiner* — Long V Le
*Assistant Examiner* — Ellsworth Weatherby
(74) *Attorney, Agent, or Firm* — Quarles & Brady, LLP (57) ABSTRACT

A system and method for improved imaging is disclosed. An exemplary system provides a peripheral ultrasound system connected to a host computer with a plug-and-play interface such as a USB. An exemplary system utilizes a dedicated graphics processing unit such as a graphics card to analyze data obtained from a region of interest to produce an image on one or more output units for the user's viewing. Based on the image displayed on the output units, the user can determine the velocity of the moving tissue and fluid. The system of the present invention can be used to produce a Doppler color flow map or for power Doppler imaging.

4 Claims, 6 Drawing Sheets

(56) References Cited

U.S. PATENT DOCUMENTS

| | | |
|---|---|---|
| 4,397,314 A | 8/1983 | Vaguine |
| 4,409,839 A | 10/1983 | Tanezer |
| 4,441,486 A | 4/1984 | Pounds |
| 4,452,084 A | 6/1984 | Taenzer |
| 4,484,569 A | 11/1984 | Driller |
| 4,513,749 A | 4/1985 | Kino et al. |
| 4,527,550 A | 7/1985 | Ruggera et al. |
| 4,528,979 A | 7/1985 | Marchenko |
| 4,567,895 A | 2/1986 | Putzke |
| 4,586,512 A | 5/1986 | Do-Huu et al. |
| 4,601,296 A | 7/1986 | Yerushalmi |
| 4,646,756 A | 3/1987 | Watmough |
| 4,663,358 A | 5/1987 | Hyon |
| 4,668,516 A | 5/1987 | Duraffourd et al. |
| 4,697,588 A | 10/1987 | Reichenberger |
| 4,757,820 A | 7/1988 | Itoh |
| 4,807,633 A | 2/1989 | Fry |
| 4,858,613 A | 8/1989 | Fry et al. |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida |
| 4,874,562 A | 10/1989 | Hyon |
| 4,875,487 A | 10/1989 | Seppi |
| 4,893,624 A | 1/1990 | Lele |
| 4,896,673 A | 1/1990 | Rose et al. |
| D306,965 S | 4/1990 | Jaworski |
| 4,917,096 A | 4/1990 | Englehart et al. |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry et al. |
| 4,955,365 A | 9/1990 | Fry et al. |
| 4,958,626 A | 9/1990 | Nambu |
| 4,976,709 A | 12/1990 | Sand |
| 4,979,501 A | 12/1990 | Valchanov |
| 5,012,797 A | 5/1991 | Liang |
| 5,036,855 A | 8/1991 | Fry et al. |
| 5,054,470 A | 10/1991 | Fry et al. |
| 5,115,814 A | 5/1992 | Griffith |
| 5,117,832 A | 6/1992 | Sanghvi et al. |
| 5,123,418 A | 6/1992 | Saurel |
| 5,143,063 A | 9/1992 | Fellner |
| 5,143,074 A | 9/1992 | Dory |
| 5,150,711 A | 9/1992 | Dory |
| 5,150,714 A | 9/1992 | Green |
| 5,156,144 A | 10/1992 | Iwasaki et al. |
| 5,158,536 A | 10/1992 | Sekins |
| 5,163,421 A | 11/1992 | Bernstein et al. |
| 5,191,880 A | 3/1993 | McLeod |
| 5,209,720 A | 5/1993 | Unger |
| 5,224,467 A | 7/1993 | Oku |
| 5,230,334 A | 7/1993 | Klopotek |
| 5,230,338 A | 7/1993 | Allen et al. |
| 5,265,614 A | 11/1993 | Hayakawa |
| 5,267,985 A | 12/1993 | Shimada et al. |
| 5,269,297 A | 12/1993 | Weng et al. |
| 5,282,797 A | 2/1994 | Chess |
| 5,295,484 A | 3/1994 | Marcus |
| 5,304,169 A | 4/1994 | Sand |
| 5,321,520 A | 6/1994 | Inga et al. |
| 5,360,268 A | 11/1994 | Hayashi |
| 5,370,121 A | 12/1994 | Reichenberger et al. |
| 5,371,483 A | 12/1994 | Bhardwaj |
| 5,380,280 A | 1/1995 | Peterson |
| 5,419,327 A | 5/1995 | Rohwedder et al. |
| 5,435,311 A | 7/1995 | Umemura |
| 5,458,596 A | 10/1995 | Lax et al. |
| 5,487,388 A | 1/1996 | Rello et al. |
| 5,492,126 A | 2/1996 | Hennige et al. |
| 5,496,256 A | 3/1996 | Bock et al. |
| 5,501,655 A | 3/1996 | Rolt et al. |
| 5,507,790 A | 4/1996 | Weiss et al. |
| 5,520,188 A | 5/1996 | Hennige et al. |
| 5,526,815 A | 6/1996 | Granz et al. |
| 5,558,092 A * | 9/1996 | Unger et al. ............ 600/439 |
| 5,601,526 A | 2/1997 | Chapelon et al. |
| 5,603,323 A | 2/1997 | Pflugrath et al. |
| 5,676,692 A | 10/1997 | Sanghvi et al. |
| 5,687,737 A * | 11/1997 | Branham et al. ............ 600/523 |
| 5,715,823 A | 2/1998 | Wood et al. |
| 5,755,753 A | 5/1998 | Knowlton |
| 5,762,066 A | 6/1998 | Law et al. |
| 5,795,297 A | 8/1998 | Daigle |
| 5,795,311 A | 8/1998 | Wess et al. |
| 5,840,032 A * | 11/1998 | Hatfield et al. ............ 600/443 |
| 5,853,367 A | 12/1998 | Chalek et al. |
| 5,871,524 A | 2/1999 | Knowlton |
| 5,873,902 A | 2/1999 | Sanghvi et al. |
| 5,904,659 A | 5/1999 | Duarte et al. |
| 5,931,805 A | 8/1999 | Brisken |
| 5,971,949 A | 10/1999 | Levin et al. |
| 5,984,882 A | 11/1999 | Rosenchein et al. |
| 6,050,943 A | 4/2000 | Slayton et al. |
| 6,071,239 A | 6/2000 | Cribbs et al. |
| 6,090,054 A | 7/2000 | Tagishi et al. |
| 6,093,883 A | 7/2000 | Sanghvi et al. |
| 6,101,407 A | 8/2000 | Groezinger |
| 6,113,558 A | 9/2000 | Rosenchein et al. |
| 6,113,559 A | 9/2000 | Klopotek |
| 6,135,971 A | 10/2000 | Hutchinson et al. |
| 6,159,150 A | 12/2000 | Yale et al. |
| 6,171,244 B1 | 1/2001 | Finger et al. |
| 6,176,840 B1 | 1/2001 | Nishimura et al. |
| 6,183,426 B1 | 2/2001 | Akisada et al. |
| 6,190,323 B1 | 2/2001 | Dias et al. |
| 6,210,327 B1 | 4/2001 | Brackett et al. |
| 6,241,753 B1 | 6/2001 | Knowlton |
| 6,287,257 B1 | 9/2001 | Matichuk |
| 6,322,509 B1 * | 11/2001 | Pan et al. ............ 600/443 |
| 6,325,540 B1 | 12/2001 | Lounsberry et al. |
| 6,325,769 B1 | 12/2001 | Klopotek |
| 6,356,780 B1 | 3/2002 | Licato et al. |
| 6,361,531 B1 | 3/2002 | Hissong et al. |
| 6,377,855 B1 | 4/2002 | Knowlton |
| 6,381,498 B1 | 4/2002 | Knowlton |
| 6,409,720 B1 | 6/2002 | Hissong |
| 6,413,254 B1 | 7/2002 | Hissong et al. |
| 6,419,648 B1 | 7/2002 | Vitek et al. |
| 6,428,532 B1 | 8/2002 | Doukas et al. |
| 6,438,424 B1 | 8/2002 | Knowlton |
| 6,443,914 B1 | 9/2002 | Constantino |
| 6,500,141 B1 | 12/2002 | Irion et al. |
| 6,595,934 B1 | 7/2003 | Hissong et al. |
| 6,607,498 B2 | 8/2003 | Eshel |
| 6,623,430 B1 | 9/2003 | Slayton et al. |
| 6,626,854 B2 | 9/2003 | Friedman et al. |
| 6,626,855 B1 | 9/2003 | Weng et al. |
| 6,638,226 B2 | 10/2003 | He et al. |
| 6,666,835 B2 | 12/2003 | Martin et al. |
| 6,692,450 B1 | 2/2004 | Coleman |
| 6,719,694 B2 | 4/2004 | Weng et al. |
| 6,733,449 B1 * | 5/2004 | Krishnamurthy et al. .... 600/437 |
| 6,749,624 B2 | 6/2004 | Knowlton |
| 6,905,466 B2 | 6/2005 | Salgo et al. |
| 6,921,371 B2 | 7/2005 | Wilson |
| 6,948,843 B2 | 9/2005 | Laugharn et al. |
| 6,974,417 B2 | 12/2005 | Lockwood et al. |
| 7,022,089 B2 | 4/2006 | Ooba et al. |
| 7,063,666 B2 | 6/2006 | Weng et al. |
| 7,115,123 B2 | 10/2006 | Knowlton et al. |
| 7,258,674 B2 | 8/2007 | Cribbs et al. |
| RE40,403 E | 6/2008 | Cho et al. |
| 7,615,015 B2 | 11/2009 | Coleman |
| 7,824,348 B2 | 11/2010 | Barthe et al. |
| 8,057,389 B2 | 11/2011 | Barthe et al. |
| 2001/0009997 A1 | 7/2001 | Pope |
| 2001/0014780 A1 | 8/2001 | Martin et al. |
| 2001/0039380 A1 | 11/2001 | Larson et al. |
| 2001/0041880 A1 | 11/2001 | Brisken |
| 2002/0000763 A1 | 1/2002 | Jones |
| 2002/0040199 A1 | 4/2002 | Klopotek |
| 2002/0040442 A1 | 4/2002 | Ishidera |
| 2002/0055702 A1 | 5/2002 | Atala |

(56) References Cited

U.S. PATENT DOCUMENTS

| | | |
|---|---|---|
| 2002/0062077 A1 | 5/2002 | Emmenegger et al. |
| 2002/0062142 A1 | 5/2002 | Knowlton |
| 2002/0082528 A1 | 6/2002 | Friedman et al. |
| 2002/0082589 A1 | 6/2002 | Friedman et al. |
| 2002/0095143 A1 | 7/2002 | Key |
| 2002/0128648 A1 | 9/2002 | Weber |
| 2002/0156400 A1 | 10/2002 | Babaev |
| 2002/0161357 A1 | 10/2002 | Anderson et al. |
| 2002/0165529 A1 | 11/2002 | Danek |
| 2002/0168049 A1 | 11/2002 | Schriever |
| 2002/0169394 A1 | 11/2002 | Eppstein et al. |
| 2002/0169442 A1 | 11/2002 | Neev |
| 2002/0173721 A1* | 11/2002 | Grunwald et al. ............ 600/437 |
| 2002/0193831 A1 | 12/2002 | Smith |
| 2003/0014039 A1 | 1/2003 | Barzell et al. |
| 2003/0018255 A1 | 1/2003 | Martin |
| 2003/0028113 A1* | 2/2003 | Gilbert et al. ............... 600/447 |
| 2003/0032900 A1 | 2/2003 | Ella |
| 2003/0036706 A1 | 2/2003 | Slayton |
| 2003/0040739 A1 | 2/2003 | Koop |
| 2003/0050678 A1 | 3/2003 | Sierra |
| 2003/0060736 A1 | 3/2003 | Martin et al. |
| 2003/0065313 A1 | 4/2003 | Koop et al. |
| 2003/0074023 A1 | 4/2003 | Kaplan |
| 2003/0083536 A1 | 5/2003 | Eshel et al. |
| 2003/0097071 A1* | 5/2003 | Halmann et al. ............. 600/459 |
| 2003/0125629 A1 | 7/2003 | Ustuner |
| 2003/0171678 A1 | 9/2003 | Batten et al. |
| 2003/0176790 A1 | 9/2003 | Slayton |
| 2003/0191396 A1 | 10/2003 | Sanghvi et al. |
| 2003/0200481 A1 | 10/2003 | Stanley |
| 2003/0212129 A1 | 11/2003 | Liu et al. |
| 2003/0212351 A1 | 11/2003 | Hissong et al. |
| 2003/0212393 A1 | 11/2003 | Knowlton et al. |
| 2003/0216795 A1 | 11/2003 | Harth |
| 2003/0220536 A1 | 11/2003 | Hissong |
| 2003/0220585 A1 | 11/2003 | Hissong |
| 2003/0236487 A1 | 12/2003 | Knowlton |
| 2004/0000316 A1 | 1/2004 | Knowlton |
| 2004/0001809 A1 | 1/2004 | Brisken |
| 2004/0002705 A1 | 1/2004 | Knowlton et al. |
| 2004/0015079 A1* | 1/2004 | Berger et al. ................ 600/437 |
| 2004/0015106 A1 | 1/2004 | Coleman |
| 2004/0030227 A1 | 2/2004 | Littrup |
| 2004/0039312 A1 | 2/2004 | Hillstead et al. |
| 2004/0039418 A1 | 2/2004 | Elstrom et al. |
| 2004/0041563 A1* | 3/2004 | Lewin et al. ................. 324/307 |
| 2004/0059266 A1 | 3/2004 | Fry et al. |
| 2004/0073079 A1 | 4/2004 | Altshuler et al. |
| 2004/0073113 A1 | 4/2004 | Salgo |
| 2004/0073116 A1* | 4/2004 | Smith .......................... 600/450 |
| 2004/0102697 A1 | 5/2004 | Evron |
| 2004/0143297 A1 | 7/2004 | Ramsey |
| 2004/0152982 A1* | 8/2004 | Hwang et al. ............... 600/441 |
| 2004/0186535 A1 | 9/2004 | Knowlton et al. |
| 2004/0206365 A1 | 10/2004 | Knowlton |
| 2004/0210214 A1 | 10/2004 | Knowlton |
| 2004/0217675 A1 | 11/2004 | Desilets et al. |
| 2004/0249318 A1 | 12/2004 | Tanaka et al. |
| 2004/0267252 A1 | 12/2004 | Washington |
| 2005/0033201 A1 | 2/2005 | Takahashi et al. |
| 2005/0055073 A1 | 3/2005 | Weber |
| 2005/0070961 A1 | 3/2005 | Maki et al. |
| 2005/0074407 A1 | 4/2005 | Smith |
| 2005/0080469 A1 | 4/2005 | Larson |
| 2005/0113689 A1* | 5/2005 | Gritzky ........................ 600/437 |
| 2005/0137656 A1 | 6/2005 | Malak |
| 2005/0154313 A1 | 7/2005 | Desilets et al. |
| 2005/0154314 A1 | 7/2005 | Quistgaard |
| 2005/0154332 A1 | 7/2005 | Zanelli |
| 2005/0187495 A1 | 8/2005 | Quistgaard et al. |
| 2005/0228281 A1* | 10/2005 | Nefos .......................... 600/446 |
| 2005/0256406 A1 | 11/2005 | Barthe |
| 2005/0261584 A1 | 11/2005 | Eshel |
| 2005/0267454 A1 | 12/2005 | Hissong et al. |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058707 A1 | 3/2006 | Barthe |
| 2006/0058712 A1 | 3/2006 | Altshuler et al. |
| 2006/0074309 A1* | 4/2006 | Bonnefous ................... 600/437 |
| 2006/0074313 A1 | 4/2006 | Slayton |
| 2006/0074314 A1 | 4/2006 | Slayton |
| 2006/0074355 A1 | 4/2006 | Slayton |
| 2006/0079816 A1 | 4/2006 | Barthe |
| 2006/0079868 A1 | 4/2006 | Makin |
| 2006/0084891 A1 | 4/2006 | Barthe |
| 2006/0089632 A1 | 4/2006 | Barthe |
| 2006/0089688 A1 | 4/2006 | Panescu |
| 2006/0111744 A1 | 5/2006 | Makin |
| 2006/0116671 A1 | 6/2006 | Slayton |
| 2006/0122508 A1 | 6/2006 | Slayton |
| 2006/0122509 A1 | 6/2006 | Desilets |
| 2006/0161062 A1* | 7/2006 | Arditi et al. .................. 600/443 |
| 2006/0184069 A1 | 8/2006 | Vaitekunas |
| 2006/0184071 A1 | 8/2006 | Klopotek |
| 2006/0206105 A1 | 9/2006 | Chopra |
| 2006/0241440 A1 | 10/2006 | Eshel et al. |
| 2006/0241442 A1 | 10/2006 | Barthe |
| 2006/0282691 A1 | 12/2006 | Barthe |
| 2006/0291710 A1* | 12/2006 | Wang et al. .................. 382/131 |
| 2007/0032784 A1 | 2/2007 | Gliklich |
| 2007/0035201 A1 | 2/2007 | Desilets et al. |
| 2007/0055154 A1 | 3/2007 | Torbati |
| 2007/0087060 A1 | 4/2007 | Dietrich |
| 2007/0088346 A1 | 4/2007 | Mirizzi et al. |
| 2007/0167709 A1 | 7/2007 | Slayton |
| 2007/0208253 A1 | 9/2007 | Slayton |
| 2008/0071255 A1 | 3/2008 | Barthe |
| 2008/0086054 A1 | 4/2008 | Slayton |
| 2008/0214966 A1 | 9/2008 | Slayton |
| 2008/0221491 A1 | 9/2008 | Slayton |
| 2008/0275342 A1 | 11/2008 | Barthe |
| 2008/0281237 A1 | 11/2008 | Slayton |
| 2008/0281255 A1 | 11/2008 | Slayton |
| 2008/0294073 A1 | 11/2008 | Barthe |

FOREIGN PATENT DOCUMENTS

| | | |
|---|---|---|
| DE | 10219217 | 11/2003 |
| DE | 20314479 | 3/2004 |
| EP | 0344773 | 12/1989 |
| EP | 1479412 | 11/1991 |
| EP | 0473553 | 4/1992 |
| EP | 0661029 | 7/1995 |
| EP | 1234566 | 8/2002 |
| EP | 1262160 | 12/2002 |
| GB | 2113099 A | 8/1983 |
| JP | 3123559 | 5/1991 |
| JP | 03136642 | 6/1991 |
| JP | 4089058 | 3/1992 |
| JP | 7080087 | 3/1995 |
| JP | 7222782 | 8/1995 |
| JP | 2002078764 | 3/2002 |
| JP | 2003050298 | 2/2003 |
| JP | 2003204982 | 7/2003 |
| JP | 2005323213 | 11/2005 |
| KR | 1020010024871 | 3/2003 |
| KR | 1020060113930 | 11/2006 |
| KR | 1020070065332 | 6/2007 |
| KR | 1020070070161 | 7/2007 |
| KR | 1020070098856 | 10/2007 |
| KR | 1020070104878 | 10/2007 |
| KR | 1020070114105 | 11/2007 |
| WO | WO9735518 | 10/1997 |
| WO | WO9832379 | 7/1998 |
| WO | WO9933520 | 7/1999 |
| WO | WO9949788 | 10/1999 |
| WO | 0015300 | 3/2000 |
| WO | WO0015300 | 3/2000 |
| WO | 0021612 | 4/2000 |
| WO | WO0021612 | 4/2000 |
| WO | 0128623 | 4/2001 |

(56) References Cited

FOREIGN PATENT DOCUMENTS

| WO | WO0128623 | 4/2001 |
|---|---|---|
| WO | 0182777 | 11/2001 |
| WO | 0182778 | 11/2001 |
| WO | 0187161 | 11/2001 |
| WO | WO0182777 | 11/2001 |
| WO | WO0182778 | 11/2001 |
| WO | WO0187161 | 11/2001 |
| WO | 0209813 | 2/2002 |
| WO | WO0209813 | 2/2002 |
| WO | 0224050 | 3/2002 |
| WO | WO0224050 | 3/2002 |
| WO | 02292168 | 11/2002 |
| WO | WO02092168 | 11/2002 |
| WO | 03065347 | 8/2003 |
| WO | 03070105 | 8/2003 |
| WO | WO03070105 | 8/2003 |
| WO | WO03077833 | 9/2003 |
| WO | 03086215 | 10/2003 |
| WO | 03099177 | 12/2003 |
| WO | 03101530 | 12/2003 |
| WO | 2005090978 | 9/2005 |
| WO | 2006036870 | 4/2006 |
| WO | 2006042168 | 4/2006 |
| WO | 2006042201 | 4/2006 |

OTHER PUBLICATIONS

P. Barthe et al, Ultrasound Therapy System and Ablation Results Utilizing Miniature Imaging/Therapy Arrays, Ultrasonics Symposium, Aug. 23, 2004, pp. 1792-1795, 2004 IEEE vol. 3.

I. Makin et al, Confirmal Bulk Ablation and Therapy Monitoring Using Intracorporeal Image-Treat Ultrasound Arrays, 4th International Symposium on Theraputic Ultrasound, Sep. 18, 2004, ISBN 0735402396.

T. Mast et al, Bulk Ablation of Soft Tissue With Intense Ultrasound: Modeling and Experiments, J. Acoust. Soc. Am, Oct. 1, 2005, pp. 2715-2724, vol. 118(4).

Daum, D.R., et al.; "Design and evaluation of a feedback based phased array system for ultrasound surgery", IEEE Transactions and Ultrasonics, Ferroelectrics and Frequency Control, IEEE USA, vol. 45, No. 2, Mar. 1998, pp. 431-438.

Sassen, Sander; "ATI's R520 architecture, the new king of the hill?", http://www.hardwareanalysis.com/content/article/1813, Sep. 16, 2005; 2 pgs.

Wasson, Scott; "NVIDIA's GeForce 7800 GTX graphics processor Power MADD", http://techreport.com/reviews/2005q2/geforce-7800gtx/index.x?pg=1, Jun. 22, 2005; 4 pgs.

Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.

Coon, Joshua et al., "Protein identification using sequential ion/ion reactions and tandem mass spectometry" Proceedings of the National Academy of Sciences of the USA, vol. 102, No. 27, Jul. 5, 2005, pp. 9463-9468.

Corry, Peter M., et al., "Human Cancer Treatment with Ultrasound", IEEE Transactions on Sonics and Ultrasonics, vol. SU-31, No. 5, Sep. 1984, pp. 444,456.

Davis, Brian J., et al., "An Acoustic Phase Shift Technique for the Non-Invasive Measurement of Temperature Changes in Tissues", 1985 Ultrasonics Symposium, pp. 921-924.

Gliklich et al., Clinical Pilot Study of Intense Ultrasound therapy to Deep Dermal Facial Skin and Subcutaneous Tissues, Arch Facial Plastic Surgery, Mar. 1, 2007, vol. 9.

Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.

Hassan et al., "Structure and Morphology of Freeze/Thawed PVA Hydrogels," Macromolecules, Mar. 11, 2000, pp. 2472-2479, vol. 33, No. 7.

Husseini et al, "The Role of Cavitation in Acoustically Activated Drug Delivery," J. Control Release, Oct. 3, 2005, pp. 253-261, vol. 107(2).

Husseini et al. "Investigating the mechanism of accoustically activated uptake of drugs from Pluronic micelles," BMD Cancer 2002, 2:20k, Aug. 30, 2002, pp. 1-6.

Jenne, J., et al., "Temperature Mapping for High Energy US-Therapy", 1994 Ultrasonics Symposium, pp. 1879-1882.

Makin et al, "Miniaturized Ultrasound Arrays for Interstitial Ablation and Imaging," UltraSound Med. Biol. 2005, Nov. 1, 2005, pp. 1539-1550, vol. 31(11).

Paradossi et al., "Poly(vinyl alcohol) as versatile biomaterial for potential biomedical applications," Journal of Materials Science: Materials in Medicine, 2003, pp. 687-691, vol. 14.

Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.

Righetti et al, "Elastographic Characterization of HIFU-Induced Lesions in Canine Livers," 1999, Ultrasound in Med & Bio, vol. 25, No. 7, pp. 1099-1113.

Sanghvi, N.T., et al., "Transrectal Ablation of Prostate Tissue Using Focused Ultrasound," 1993 Ultrasonics Symposium, IEEE, pp. 1207-1210.

Seip, Ralf, et al., "Noninvasive Detection of Thermal Effects Due to Highly Focused Ultrasonic Fiels," IEEE Symposium, pp. 1229-1232, vol. 2, Oct. 3-Nov. 1993.

Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.

Smith, Nadine Barrie, et al., "Non-Invasive In Vivo Temperature Mapping of Ultrasound Heating Using Magnetic Resonance Techniques", 1994 Ultrasonics Symposium, pp. 1829-1832, vol. 3.

Surry et al., "Poly(vinyl alcohol) cryogel phantoms for use in ultrasound and MR imaging," Phys. Med. Biol., Dec. 6, 2004, pp. 5529-5546, vol. 49.

Syka J. E. P. et al., "Peptide and Protein Sequence Analysis by Electron Transfer Dissociation Mass Spectometry," Proceedings of the National Academy of Sciences of USA, National Academy of Aceince, Washington, DC, vol. 101, No. 26, Jun. 29, 2004, pp. 9528-9533.

Ueno, S., et al., "Ultrasound Thermometry in Hyperthermia", 1990 Ultrasonic Symposium, pp. 1645-1652.

Wang, H., et al., "Limits on Focused Ultrasound for Deep Hyperthermia", 1994 Ultrasonic Symposium, Nov. 1-4, 1994, pp. 1869-1872, vol. 3.

White et al "Selective Creation of Thermal Injury Zones in the Superficial Musculoaponeurotic System Using Intense Ultrasound Therapy," Arch Facial Plastic Surgery, Jan./Feb. 2007, vol. 9, No. 1.

Chen, L. et al., "Effect of Blood Perfusion on the ablation of liver perenchyma with high intensity focused ultrasound," Phys. Med. Biol; 38:1661-1673; 1993b.

(56) References Cited

OTHER PUBLICATIONS

Damianou et al., "Application of the Thermal Dose Concept for Predicting the Necrosed Tissue Volume During Ultrasound Surgery," 1993 IEEE Ultrasound Symposium, pp. 1199-1202.

Fry, W.J. et al., "Production of Focal Destructive Lesions in the Central Nervous System with Ultrasound," J. Neurosurg., 11:471-478; 1954.

Harr, G.R. et al., "Tissue Destruction with Focused Ultrasound in Vivo," Eur. Urol. 23 (suppl. 1):8-11; 1993.

Jeffers et al., "Evaluation of the Effect of Cavitation Activity on Drug-Ultrasound Synergisms," 1993 IEEE Ultrasonics Symposium, pp. 925-928.

Madersbacher, S. et al., "Tissue Ablation in Bening Prostatic Hyperplasia with High Intensity Focused Ultrasound," Dur. Urol., 23 (suppl. 1):39-43; 1993.

Saad et al., "Ultrasound-Enhanced Effects of Adriamycin Against Murine Tumors," Ultrasound in Med. & Biol. vol. 18, No. 8, pp. 715-723 (1992).

Simon et al., "Applications of Lipid-Coated Microbubble Ultrasonic Contrast to Tumor Therapy," Ultrasound in Med. & Biol. vol. 19, No. 2, pp. 123-125 (1993).

Talbert, D. G., "An Add-On Modification for Linear Array Real-Time Ultrasound Scanners to Produce 3D Displays," UTS Int'l 1977 Brighton, England (Jun. 28-30, 1977) pp. 57-67.

Tata et al., "Interaction of Ultrasound and Model Membrane Systems: Analyses and Predictions," American Chemical Society, Phys. Chem. 1992, 96, pp. 3548-3555.

* cited by examiner

ULTRASOUND SYSTEM AND METHOD FOR IMAGING AND/OR MEASURING DISPLACEMENT OF MOVING TISSUE AND FLUID

FIELD OF INVENTION

The present invention relates to imaging and treatment systems, and in particular to an improved ultrasound system for imaging and/or measuring the displacement of moving tissue and fluid.

BACKGROUND OF THE INVENTION

Ultrasound technology is an efficient and accurate way to examine and measure internal body structures and detect bodily abnormalities. Ultrasound technology works by emitting high frequency sound waves into a region of interest. The sound waves are emitted from a probe, strike the region of interest, and then reflect back to the probe. For example, certain sound waves strike tissues or fluid in the region of interest before other sound waves do and are thus reflected back to the probe sooner than other sound waves. The ultrasound machine measures the difference in time for various ultrasonic waves to be emitted and reflected back to the transducer probe and produces a picture of the region of interest based on those time differences.

Besides producing an image of the region of interest, ultrasound is capable of determining the velocity of moving tissue and fluids. For example, an ultrasound user can observe a patient's blood as it flows through the heart, determine the speed or flow rate of the blood's movement, and whether the blood is moving towards or away from the heart.

One method of measuring velocity of moving tissue and fluid is the use of Doppler ultrasound with color mapping. Doppler ultrasound is based upon the Doppler effect. When the object reflecting the sound waves is moving, it changes the frequency of the echoes that are reflected back to the probe. A Doppler ultrasound machine measures the change in frequency of the sound wave echoes and calculates how fast a particular object is moving within the region of interest. Doppler color flow mapping utilizes color to depict the directional movement of tissue and fluid (such as blood) within the region of interest. Color flow mapping produces a two-dimensional image in color with flow towards the probe shown in one color and flow away from the probe shown in another color.

Another method for measuring the displacement of moving tissue and fluid is power Doppler imaging. Power Doppler imaging is similar to color flow mapping in that is can produce an image that shows the presence or absence of blood flow and the directional movement of the flow. Power Doppler is advantageous because it is up to five times more sensitive in detecting blood flow and other forms of tissue and fluid movement than color mapping. But, power Doppler imaging is not used to determine the velocity of the moving tissue and fluid.

Ultrasound equipment used for ultrasound imaging and treatment can be divided into three main components. First, there is a peripheral ultrasound system that comprises a probe with a transducer array or a single element for emitting ultrasound waves and equipment that produces and conditions the ultrasound waves for emission from the probe. Second, a host computer system connected to the peripheral ultrasound system serves as to interface with the ultrasound user. Specifically, the host computer comprises a keyboard or other equipment to help control the ultrasound equipment and a monitor to display the image to the user. Finally, known ultrasound equipment comprises a microprocessor within, or connected to, the host computer.

The microprocessor is the "brain" of an ultrasound system because it performs all the computing tasks to covert the data collected at the peripheral ultrasound system into the images shown on the monitor to the user. In a Doppler ultrasound system with color flow mapping, the microprocessor will process all the data and generate the velocities of the moving tissues and fluid as well as associated colors to show the directional movement of the tissues and fluid.

To properly process this data, the microprocessor comprises memory and software. The software utilizes known algorithms to measure the velocity and to chart the color of the tissue and fluid to depict the directional movement of the tissue and fluid.

Unfortunately, known Doppler ultrasound systems have numerous disadvantages. Microprocessors are not capable of quickly processing the vast information obtained during a Doppler ultrasound. Color flow mapping complicates the problem because producing color images requires a large memory and the processing capabilities that are not appropriate for processing by known microprocessors. Another drawback with Doppler ultrasound systems is despite their accuracy, they are relatively slow in producing images.

Another problem with known ultrasound equipment is the interface between the peripheral ultrasound equipment and the host computer. Specifically, known ultrasound machines utilize an uncommon type of interface which requires the user to modify his personal computer to use it as a host computer.

SUMMARY OF THE INVENTION

A system and method for ultrasound imaging and/or measurement of displacement of tissue and fluid movement is disclosed. An exemplary embodiment of a system for diagnostic imaging and measurement of displacement of living tissue utilizes a dedicated graphics processing unit to process data obtained by a peripheral ultrasound system. Additionally, the system provides a common interface for connecting the peripheral ultrasound system to the host computer.

In accordance with an exemplary embodiment, the dedicated graphics processing unit comprises a dedicated graphics card with an associated video memory and graphics processor configured to process the data obtained by the peripheral ultrasound system. The graphics card further comprises software that utilizes various algorithms to process the data, examples of which include a Doppler shift algorithm and/or a CFM algorithm and the like.

In accordance with an exemplary embodiment, the peripheral ultrasound system comprises a transducer probe with a single element or an array to emit ultrasound waves. Further, the peripheral ultrasound system can comprise a beamforming system that focuses the ultrasound beam prior to emission from the transducer probe. In this exemplary embodiment, the beamforming system also conditions the ultrasound energy prior to emission from the probe by incorporating a conditioning circuit. The peripheral ultrasound system can also comprise a processing device such as a demodulator to process ultrasound waves that have been reflected back to the probe into computer readable data.

In accordance with an exemplary embodiment, the peripheral ultrasound system combines Doppler imaging with B-Flow imaging. This combination increases the speed of image production, yet it does not diminish the quality of images produced by the system.

In accordance with an exemplary embodiment, a common interface between the host computer and peripheral ultrasound system is provided. The common interface can be any type of interface used on personal computers that enables a personal computer to be connected to the peripheral ultrasound system. In one exemplary embodiment, a plug-and-play style interface is used, such as a Universal Serial Bus (USB) interface.

In accordance with an exemplary embodiment, ultrasound energy is conditioned within the beamforming device, transmitting from the transducer probe to the region of interest, reflected back to the transducer probe, demodulated by the demodulator into data readable by the host computer, delivered to the host computer through a USB interface as computer readable data, and processed by the dedicated graphics processing unit to determine the velocity of the moving tissue and fluid.

BRIEF DESCRIPTION OF THE DRAWINGS

The subject matter of the invention is particularly pointed out in the concluding portion of the specification. The invention, however, both as to organization and method of operation, may be best understood by reference to the following description taken in conjunction with the accompanying drawing figures, in which like parts may be referred to by like numerals.

DETAILED DESCRIPTION

The present invention may be described herein in terms of various functional components and processing steps. It should be appreciated that such components and steps may be realized by any number of hardware components configured to perform the specified functions. For example, the present invention may employ various visual imaging and display devices used for medical treatment which may carry out a variety of functions under the control of one or more control systems or other control devices. In addition, the present invention may be practiced in any number of imaging and medical contexts and that the exemplary embodiments relating to an ultrasound system and method as described herein are merely indicative of exemplary applications for the invention. For example, the principles, features and methods discussed may be applied to any imaging or medical application. Further, various aspects of the present invention may be suitably applied to other applications that utilize imaging technology.

Figure 1:
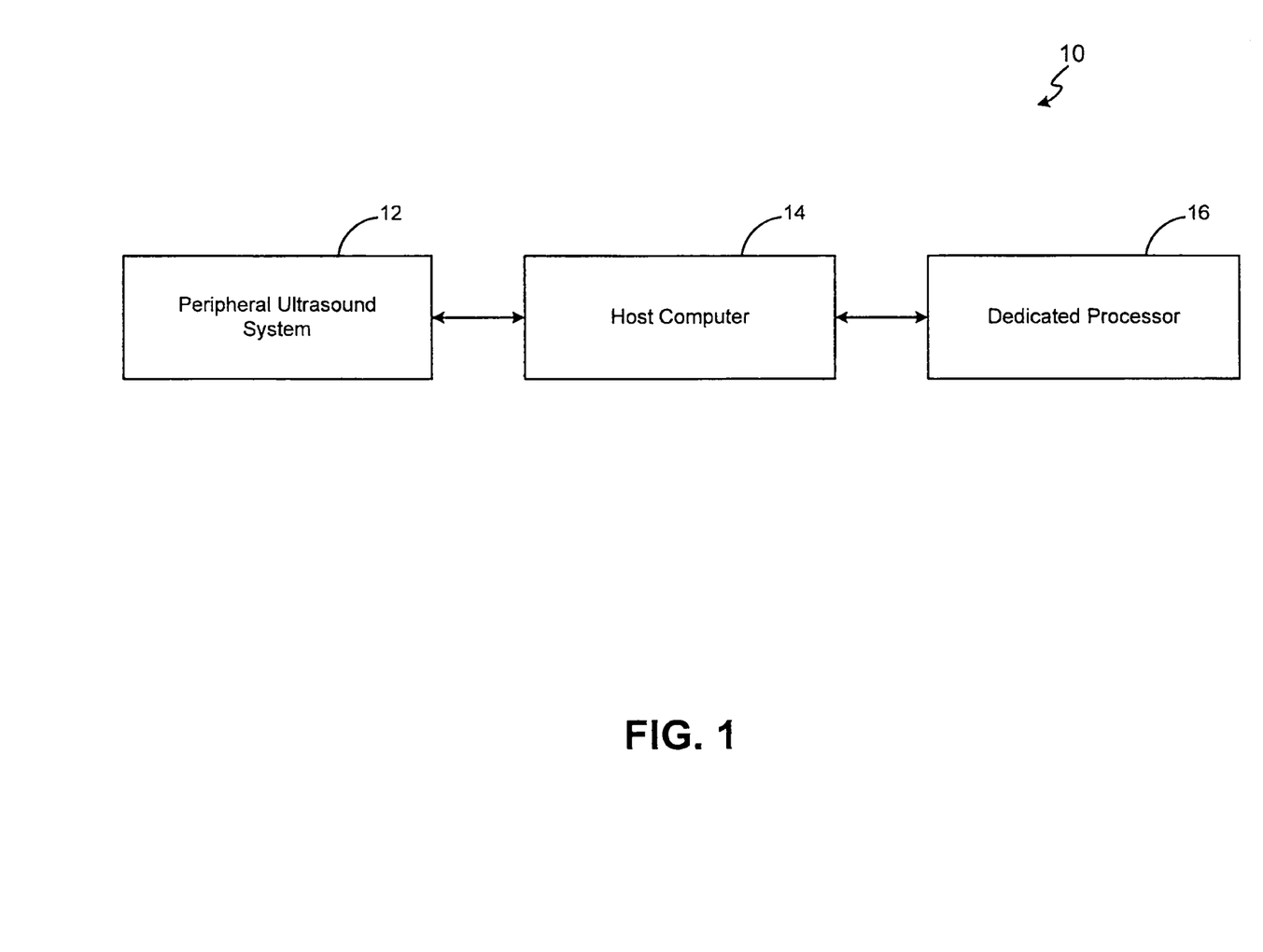
FIG. 1 illustrates a block diagram of an ultrasound system in accordance with an exemplary embodiment of the present invention.

An exemplary system for ultrasonic imaging and/or measurement of displacement of moving tissue and fluid denoted throughout as system 10 is provided. The system of the present invention can be used in traditional gray-scale ultrasound imaging or for color-mapping imaging. In an exemplary embodiment, system 10 is an ultrasound treatment system and comprises a peripheral ultrasound system 12 for emitting and receiving energy that is connected to and in operative communication with a host computer 14. System 10 further comprises a graphics processing unit 16 that is dedicated to process data obtained by peripheral ultrasound system 12.

Figure 3:
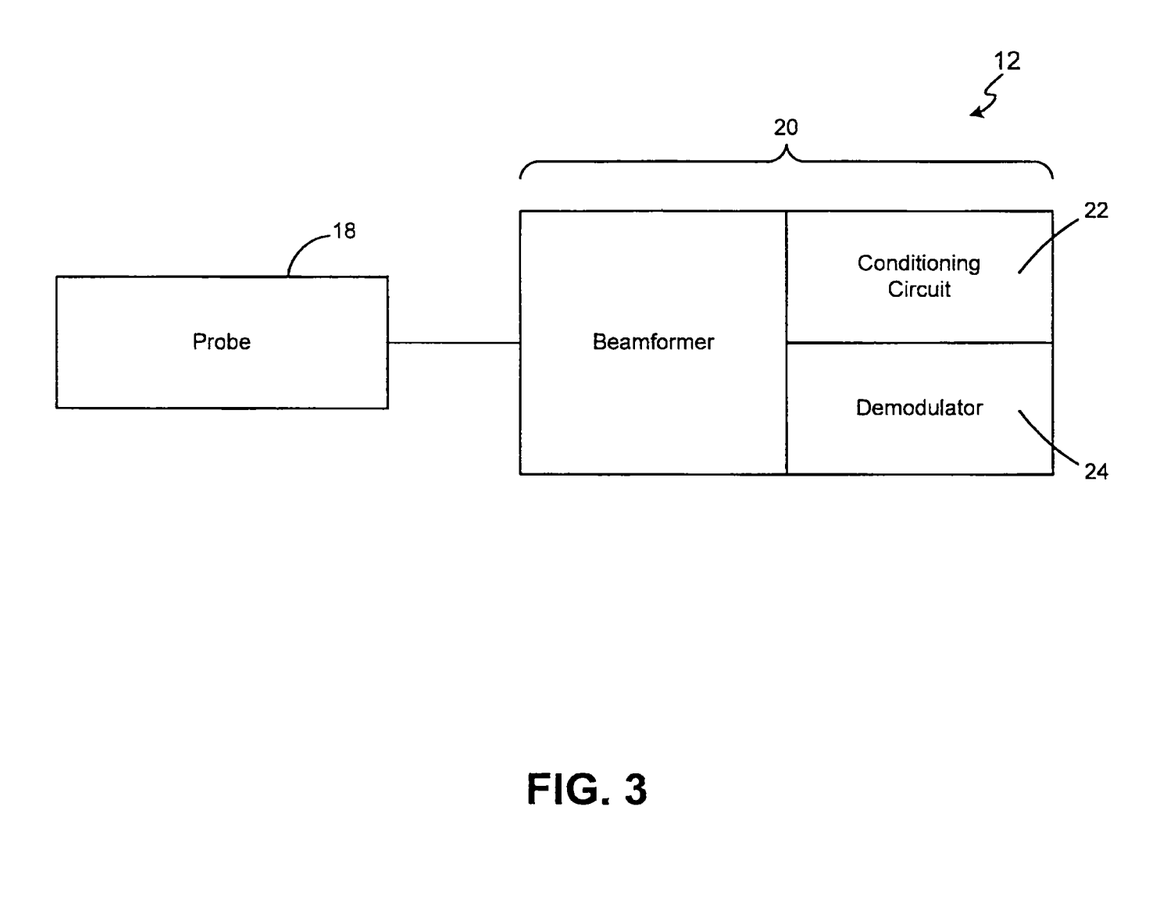
FIG. 3 illustrates a block diagram of the peripheral ultrasound system in accordance with an exemplary embodiment of the present invention.

With reference to FIG. 3, peripheral ultrasound system 12 comprises a probe 18 that transmits and receives energy. While a peripheral ultrasound system is specifically mentioned herein, any peripheral system that emits energy can be used and fall within the scope of the present invention. An exemplary energy transmitted and received by probe 18 is ultrasound energy which can be either focused or unfocused. Additionally, an exemplary probe 18 is a transducer probe that contacts a region of interest 19 on a patient or other subject that the user wishes to scan. Peripheral ultrasound system 12 also comprises beamforming device 20 for focusing the ultrasound energy before it is emitted from probe 18.

Examples of exemplary ultrasound systems are disclosed in U.S. Pat. No. 6,440,071 entitled "Peripheral Ultrasound Imaging System", U.S. patent application Ser. No. 10/944,499 entitled "Method and System For Ultrasound Treatment With A Multi-Directional Transducer", U.S. application Ser. No. 10/944,500 entitled "System and Method For Variable Depth Ultrasound Treatment", and U.S. application Ser. No. 11/163,148 entitled "Method and System For Controlled Thermal Injury of Human Superficial Tissue." All four of these patents and patent applications are hereby incorporated by reference.

In an exemplary embodiment, a conditioning circuit 22 or other similar conditioning device and a demodulator 24 are part of beamforming device 20. Demodulator 24 demodulates ultrasound energy received by probe 18 into data that is readable by host computer 14 and processed by graphics processing unit 16. Therefore, the ultrasound energy's conditioning and demodulation occurs within beamforming device 20.

An exemplary probe 18 can be configured in various manners and comprise a number of reusable or disposable components and parts in various embodiments to facilitate its operation. For example, probe 18 can be configured within any type of probe housing or arrangement for facilitating the contact of probe 18 to the patient's skin at region of interest 19, with such housing comprising various shapes, contours and configurations. Probe 18 may also comprise cables and connectors; motion mechanisms, motion sensors and encoders; thermal monitoring sensors; or user control and status related switches, and indicators such as LEDs.

In an exemplary embodiment, probe 18 includes a single transduction element mounted within probe 18. The transduction element can comprise a piezoelectrically active material, such as lead zirconante titanate (PZT), or any other piezoelectrically active material, such as a piezoelectric ceramic, crystal, plastic, or composite materials, as well as lithium niobate, lead titanate, barium titanate, or lead metaniobate. In addition to, or instead of, a piezoelectrically active material, probe 18 can comprise other materials configured for generating radiation or acoustical energy. In other exemplary embodiments, probe 18 includes a transducer array.

Lenses can also be used in the emission of ultrasound waves from probe 18. Lenses or other transduction elements can be configured to be concave, convex, or planar. For example, in one exemplary embodiment, the transduction element is configured to be concave in order to provide focused energy for treatment of region of interest 19. Additional embodiments are disclosed in U.S. patent application Ser. No. 10/944,500, entitle "Variable Depth Transducer System and Method", which is herein incorporated by reference.

An exemplary peripheral ultrasound system 12 is depicted in FIG. 3 and shows probe 18 as a separate element from beamforming device 20 and its related components. While probe 18 can be a separate element as shown, it should be noted that beamforming device 20 and its related components can be placed within probe 18 in other exemplary embodiments. Moreover, any type of transducer probe or similar device can be used and fall within the scope of the present invention.

Peripheral ultrasound system 12 is connected to host computer 14 by an interface 28 that is described in more detail below and depicted in. Host computer 14 enables the user of system 10 to view images obtained at region of interest 19, provide estimations of moving tissue and fluid displacement within region of interest 19, and to control and adjust system 10. Host computer 14 can be any type of computer system suitable for imaging applications. Exemplary computers include personal computers and laptop computers.

Figure 2:
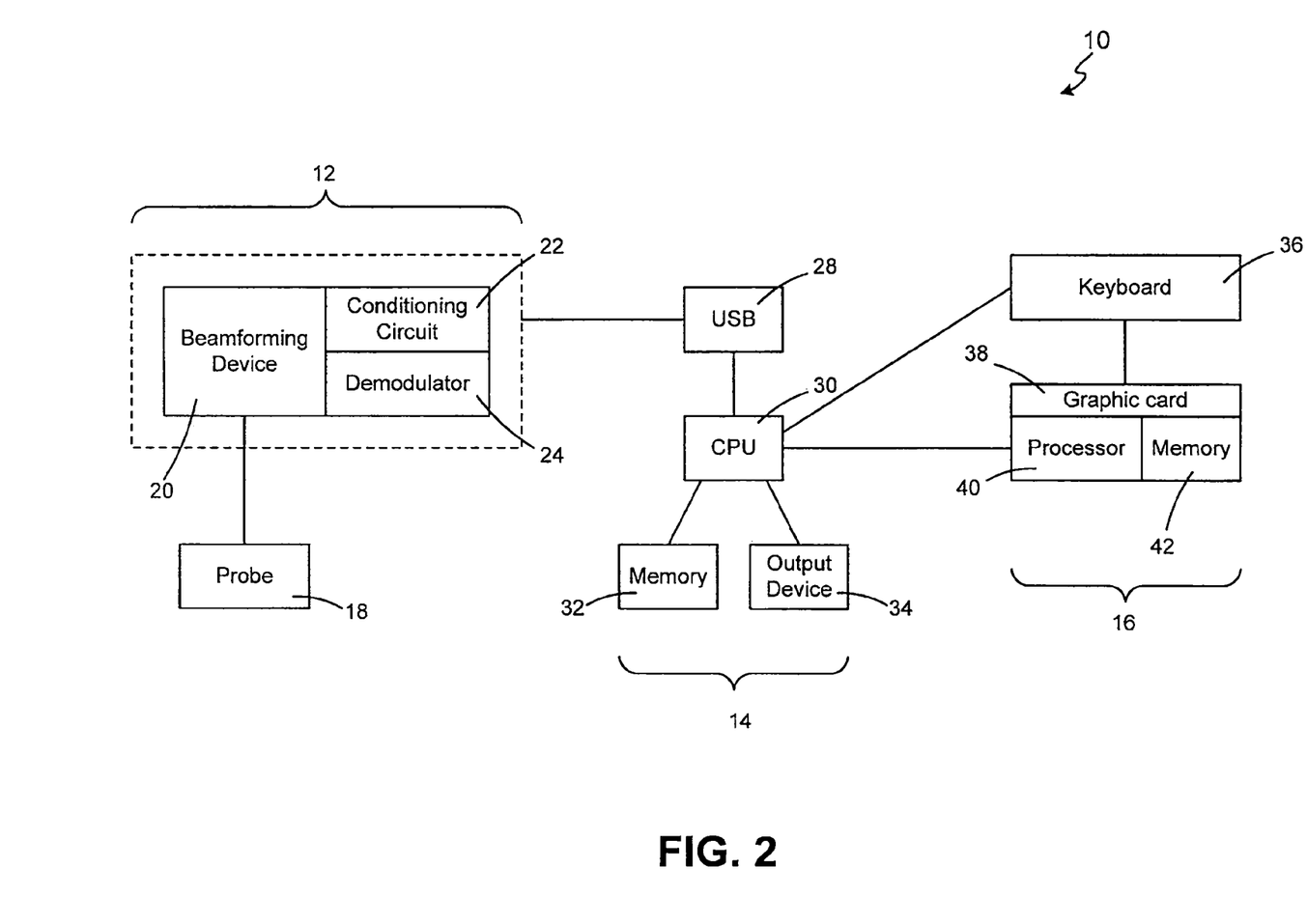
FIG. 2 illustrates a block diagram of the peripheral ultrasound system, the host computer, and the graphics processing unit in accordance with an exemplary embodiment of the present invention.

With additional reference to FIG. 2, host computer 14 comprises a central processing unit (CPU) 30 and a memory 32. While any type memory 32 can be used, an exemplary memory is a cine memory. Host computer 14 further comprises at least one output device 34 to provide the user of system 10 with an image of region of interest 19. In addition to displaying an image to the user, output device 34 enables the user to view the directional movement or obtain the velocity of the moving tissue and fluid such as blood within region of interest 19. An exemplary output 34 device is a color computer monitor that is capable of visually displaying a color flow map of region of interest 19 as described below. Further, in certain exemplary embodiments, multiple output devices 34 can be attached to CPU 30.

Figure 4:
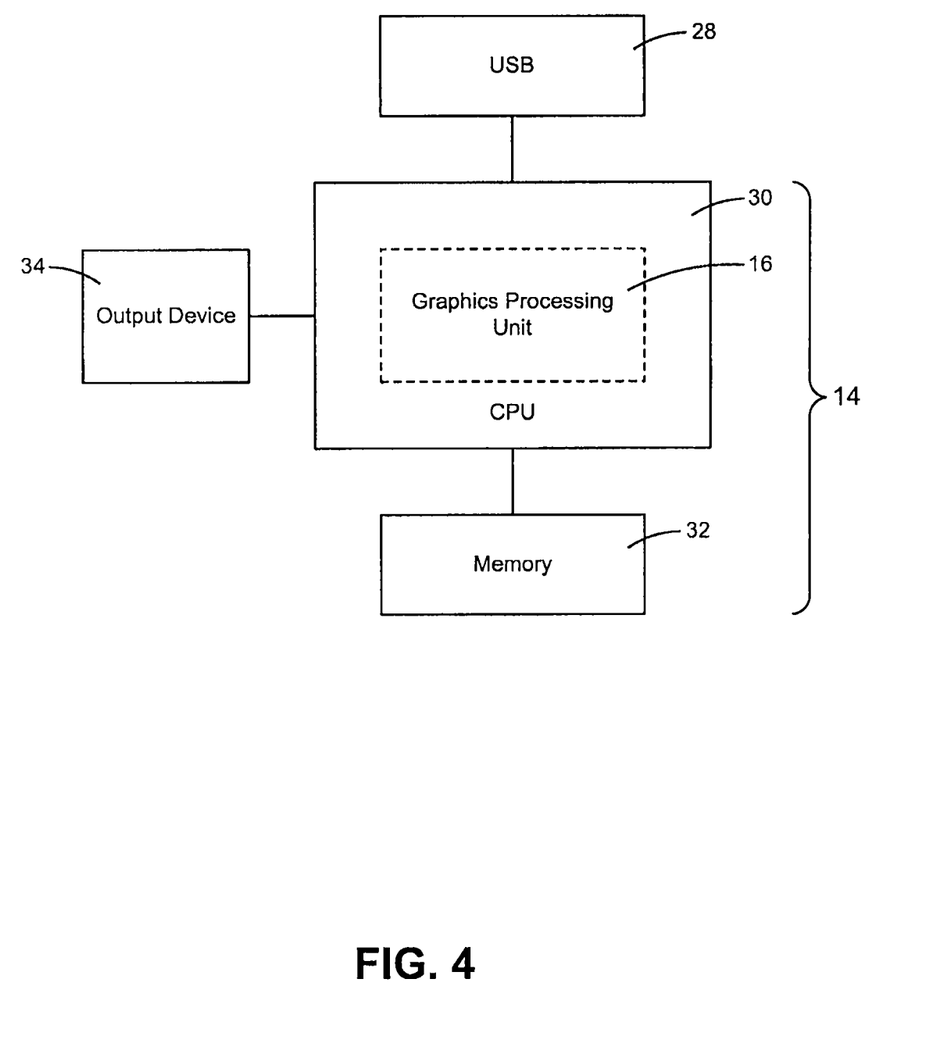
FIG. 4 illustrates a block diagram of the host computer in accordance with an exemplary embodiment of the present invention.

As shown in FIG. 4, host computer 14 further comprises control devices to enable the user to control system 10. Exemplary control devices include a keyboard 36 and a computer mouse. Other exemplary control devices include joysticks and other similar control devices and systems.

As noted above, host computer 14 is connected to peripheral ultrasound system 12 by interface 28. While any type of wired or wireless interface 28 can be used, a plug-and-play interface 28 is used in an exemplary embodiment. A plug-and-play interface 28 enables the user to quickly connect and disconnect peripheral ultrasound system 12 to host computer 14. An exemplary plug-and-play interface 28 is known as a "hot-plug capable" interface 28 in that it can enable the user of system 10 to plug peripheral ultrasound system 12 into host computer 14 without having to shut down and reboot host computer 14. These types of interfaces 28 include a Universal Serial Bus (USB) interface 28. Exemplary USB interfaces include an A type and B type USB interface.

Unlike traditional ultrasound systems that rely on a microprocessor to process the data obtained by peripheral ultrasound system 12, system 10 utilizes a dedicated graphics processing unit 16 to process the data. This enables system 10 to have a dedicated processing device for processing the large amount of data collected at peripheral ultrasound system 12 and more efficiently displaying an image on output device 34 than a microprocessor. In an exemplary embodiment, graphics processing unit 16 is dedicated solely to the function of processing data obtained by peripheral ultrasound system 12.

Figure 5:
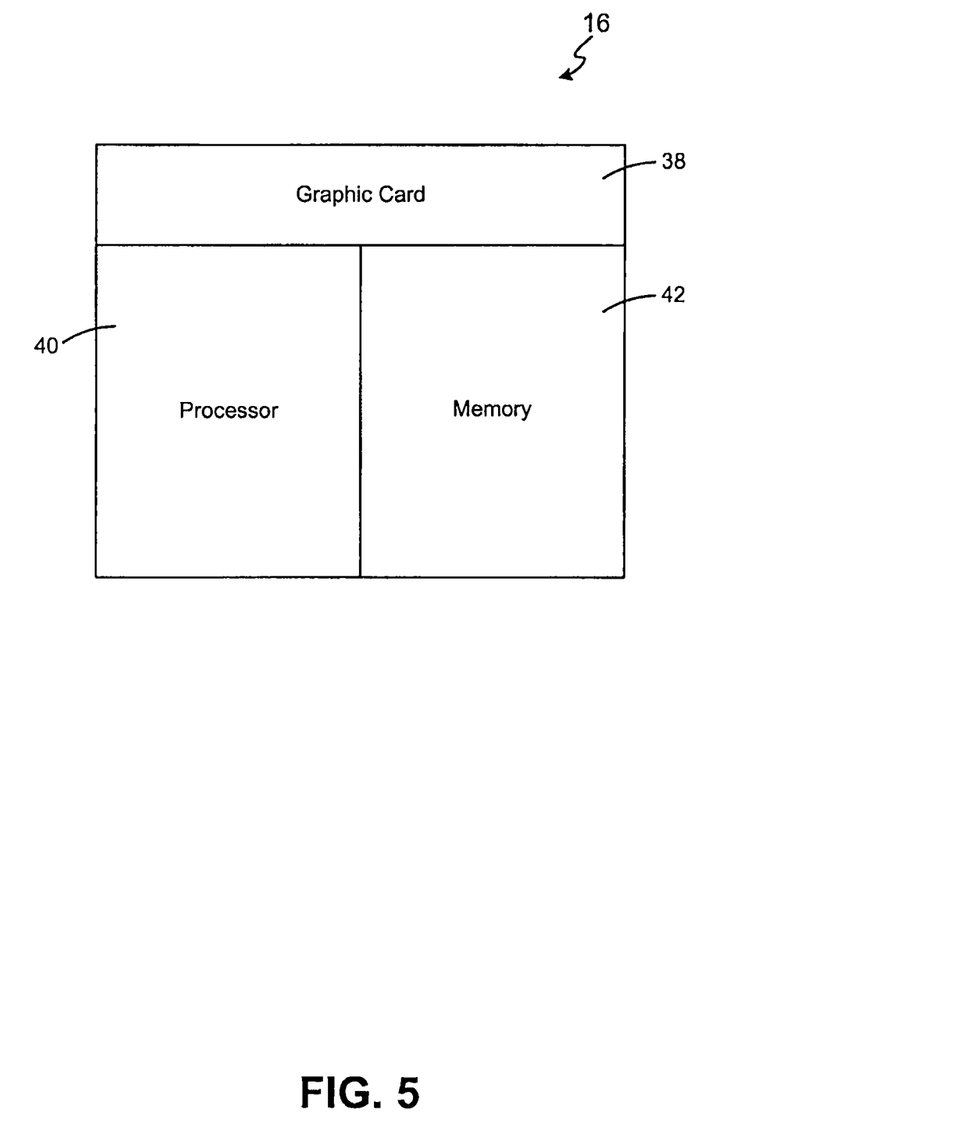
FIG. 5 illustrates a block diagram of the graphics processing unit in accordance with an exemplary embodiment of the present invention.

It should be noted that while the term "graphics processing unit" can comprise any dedicated processing device or combinations of devices that process data. An exemplary dedicated processing device is depicted in FIG. 5.

In one exemplary embodiment, graphics processing unit 16 comprises graphics card 38. In another exemplary embodiment, graphics processing unit 16 comprises a physics processing unit (PPU).

In another exemplary embodiment, graphics processing unit 16 could be a combination of a graphics card 38 and a PPU. A PPU performs nearly identical functions as graphics processing unit 16 except that a PPU is capable of processing physics code and removing the load that calculating physics puts on the graphics processing unit 16 and allocate it to the PPU. Therefore, in an exemplary embodiment, graphics processing unit 16 would comprise two devices, one being the graphics card 38 and the other a PPU. Graphics card 38 in combination with the PPU increases the efficiency and accuracy of system 10.

Other exemplary processing devices include systems that are dedicated to process the graphics data obtained by ultrasound system 12. For example, a system of a card and processor chip could be an exemplary graphics processing unit 16. Alternatively, any other dedicated chip, processor, or combination thereof can be utilized as graphics processing unit 16.

In accordance with an exemplary embodiment, graphics processing unit 16 can comprise a graphics card 38 with a processor 40 and a memory 42. For example, exemplary graphics cards 38 can comprise those produced by the NVIDIA Corporation of Santa Clara, Calif. and/or ATI Technologies, Inc. of Ontario, Canada. In an exemplary embodiment, multiple graphics cards 38 can be used to process data. In one embodiment, the image is split into two portions and a single graphics card 38 is used to process each portion.

In an exemplary embodiment, graphics processing unit 16 processes the data obtained by peripheral ultrasound system 12 by utilizing software with algorithms that are programmed within memory 42. One exemplary algorithm is the Doppler shift algorithm; however, various other algorithms can also be used.

System 10 can utilize certain imaging techniques in addition to or instead of Doppler imaging. Certain exemplary techniques include various decorrelation of frames techniques. One exemplary technique is B-flow imaging. B-flow imaging can be used by itself by system 10 or it can be combined with other techniques such as Doppler imaging. In an exemplary embodiment, system 10 combines various Doppler techniques with B-flow techniques to increase the speed and accuracy of images produced by system 10. One advantage of this increase in speed and accuracy is the ability to use a single transduction element within probe 18.

Figure 6:
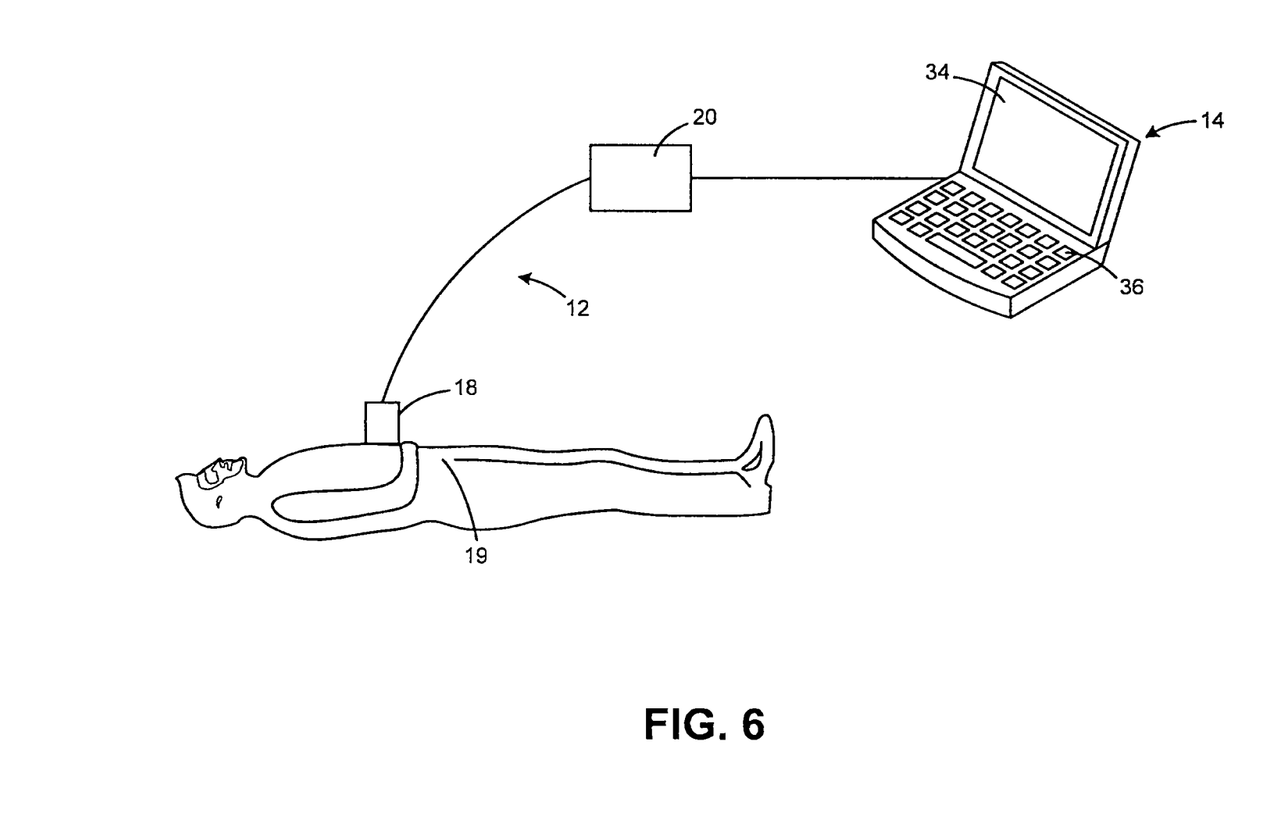
FIG. 6 illustrates the ultrasound system in use in an exemplary embodiment of the present invention.

Turning now to FIG. 6, system 10 is used to obtain images of region of interest 19. In exemplary embodiments, ultrasound images can be obtained and an estimation of displacement of moving tissue including fluid is obtained by use of system 10.

When system 10 is used for Doppler color flow mapping, the user can determine the velocity of the moving tissue and fluid as well as obtain an image of region of interest 19. Specifically, graphics processing unit 16 processes the data obtained by peripheral ultrasound system 12 and produces an image displayed on output device 34 that includes the speed of the moving tissue and fluid. In certain exemplary embodiments, the image is shown in traditional gray-scale imaging.

In other exemplary embodiments, ultrasound system 12 produces a color map to show the direction of fluid and tissue movement. The directional movement either towards or away from probe is shown on output device 34 in contrasting colors. In an exemplary embodiment, tissue and fluid moving towards the probe could be shown in shades of blue and tissue and fluid moving away from probe 18 could be shown in shades of red.

If system 10 is used to generate an image and obtain and estimation of tissue displacement using power Doppler imaging an image detailing the presence or absence of blood flow is displayed on output device 34. By viewing that image, the user can determine the directional movement of the blood flow or other moving tissue using the power Doppler imaging technique. In an exemplary embodiment, B-Flow imaging is combined with power Doppler imaging to increase speed and efficiency.

An exemplary process of obtaining an image and measuring displacement of tissue movement begins with a user connecting peripheral ultrasound system 12 to host computer 14 with interface 28. In an exemplary embodiment, the user simply plugs one end of a USB connector provided on peripheral ultrasound system 12 into the corresponding USB connector located on host computer 14.

Probe 18 is placed on the patient's skin and the transduction element produces ultrasound energy which is conditioned by conditioning circuit 22 and focused by beamforming device 20 before being emitted from probe 18. The ultrasound energy waves enter region of interest 19 and are reflected and echoed back to probe 18. These reflected ultrasound waves are demodulated into computer readable data by demodulator 24 and sent to host computer 14 via interface 28.

Once the computer data has arrived at host computer 14, it is processed by graphics processing unit 16. Specifically, graphics processing unit 16 uses an algorithm to generate an image and measure displacement of the tissue or fluid movement, e.g., by producing a color flow map or gray-scale image and/or implementing a power Doppler technique. The image is displayed on output device 34 for the user's viewing. If multiple output devices 34 are used, the image is displayed on all of them. The user can then view the image and obtain an estimate of the moving tissue's displacement.

The present invention may be described herein in terms of various functional components and processing steps. It should be appreciated that such components and steps may be realized by any number of hardware components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical contexts and that the exemplary embodiments relating to a system as described herein are merely indicative of exemplary applications for the invention. For example, the principles, features and methods discussed may be applied to any medical application. Further, various aspects of the present invention may be suitably applied to other applications, such as other medical or industrial applications.

What is claimed is:

1. A method of obtaining a diagnostic image and estimating the displacement of moving tissue and fluid, the method comprising:
    coupling a transducer probe to a region of interest;
    transmitting ultrasound energy from the transducer probe to the region of interest;
    receiving reflected ultrasound energy from the region of interest at the transducer probe, the reflected ultrasound energy comprising at least a portion of the ultrasound energy transmitted by the probe;
    delivering the reflected ultrasound energy received by the transducer probe to a demodulator for demodulation into data readable by a central processing unit of a host computer;
    delivering the data to the central processing unit;
    delivering the data to a dedicated graphics processing unit from the central processing unit;
    processing the data on the dedicated graphics processing unit and not on the central processing unit, the processing comprising
    estimating a displacement of moving tissue and fluid in the region of interest.

2. The method according to claim 1 further comprising sending a color flow map to the central processing unit from the dedicated graphics processing unit.

3. The method according to claim 1 wherein the dedicated, graphics processing unit is configured to enable the transducer to utilize a power Doppler ultrasound technique.

4. The method according to claim 1 wherein the dedicated graphics processing unit comprises a Doppler shift algorithm.

* * * * *